United States Patent [19]

Tomita et al.

[11] Patent Number: 4,971,814

[45] Date of Patent: Nov. 20, 1990

[54] WATER-SOLUBLE DIETARY FIBERS AND METHOD FOR PREPARATION OF SAME

[75] Inventors: Mamoru Tomita, Yokohama; Joji Ono, Chiba; Yasuo Fukuwatari, Kawasaki; Teruhiko Mizota, Tokyo; Kazuyoshi Nanba, Kawasaki, all of Japan

[73] Assignee: Morinaga Milk Industry Co., Ltd., Tokyo, Japan

[21] Appl. No.: 459,327

[22] Filed: Dec. 29, 1989

[30] Foreign Application Priority Data

Feb. 27, 1989 [JP] Japan ................................. 1-43202

[51] Int. Cl.$^5$ .............................................. A23L 1/214
[52] U.S. Cl. ........................................ 426/52; 426/48; 426/615; 426/637; 426/648; 426/658
[58] Field of Search ..................... 426/48, 52, 49, 615, 426/648, 637, 658

[56] References Cited

FOREIGN PATENT DOCUMENTS 1005757 1/1986 Japan ................................. 426/52
3287457 11/1988 Japan ................................. 426/52

*Primary Examiner*—Marianne Cintins
*Attorney, Agent, or Firm*—Oblon, Spivak, McClelland, Maier & Neustadt

[57] ABSTRACT

Dietary fibers having average molecular weight of 2,000–15,000, which are prepared by partially hydrolyzing polysaccharides of Konnyaku powder with a cellulase derived from microorganisms belonging to the genus Aspergillus, which are readily soluble in water, which do not prevent adsorption of useful minerals such as calcium in the digestive tract, and which do not give rise to diarrhea when an excessive amount thereof is ingested.

2 Claims, No Drawings

WATER-SOLUBLE DIETARY FIBERS AND METHOD FOR PREPARATION OF SAME

FIELD OF THE INVENTION

The present invention relates to dietary fibers which are readily soluble in water, which do not prevent adsorption of useful minerals such as calcium in the digestive tract, and which do not give rise to diarrhea when an excessive amount thereof is ingested, and a method for preparation of same.

The water-soluble dietary fibers in accordance with the present invention can be utilized as an additive to processed foods and drinkables. In other words, the water-soluble dietary fibers in accordance with the present invention can be utilized for preparation of processed foods and drinkables.

BACKGROUND OF THE INVENTION

Recently it has been indicated that there is a correlation between decrease in quantity of ingestion of fibers due to the tendency of increased uptake of highly refined foods and increase of various symptoms or diseases such as constipation, irregularity of defecation, disturbance of intestinal flora, carcinoma of colon, hypertension, diabetes mellitus and others. For this reason, it is recommended to take much more quantity of dietary fibers.

Konnyaku is a kind of plant belonging to the family of Araceae (*Amorphophallus konjac*) and have been cultivated in Japan, China and other Asian countries, and Konnyaku powder is prepared by drying smashed tubers of Amorphophallus konjac. Konnyaku powder is sold in the market as the ingredient for a traditional food called konnyaku (devil's tongue: a paste made from the polysaccharides prepared from tubers of *Amorphophallus konjac*). Konnyaku powder has been utilized as water soluble dietary fibers or a material for preparation of natureal food of low-calorie, since it contains glucomannan, in a high concentration up to about 80% (by weighte), which comprises water-soluble polysaccharides and is hardly digestible in human intestine (cf. "Chemistry of polysaccharide" page 280, 1955, Kyohritsu Shuppan Kabushiki Kaishae.

More particularly, it has been reported that when Konnyaku powder is ingested, the dietary fibers thereof may reach to the large intestine without being subjected to digestion in the small intestine, and they are excreted. It has been also reported that cholesterol, derived from foods and bile acid, is absorbed in Konnyaku powder and coincidently excreted. Thus Konnyaku is powder effective to decrease serum cholesterol level. Moreovr, Konnyaku powder is effective to adjust intestinal functions or maintain the good intestinal conditions and to manifest growth promoting activity of Bifidobacteria (Kiriyama et al, Journal of Nutrition, Vol. 97, page 382, 1968; Mizutani et al, "Intestinal Flora and Nutrition", page 89, 1983, Gakukai Shuppan Center).

Also it is reported that the dietary fibers in Konnyaku powder may swell in its aqueous solution to hold a surprisingly huge quantity of water amounting to hundreds times of itself and that when the dietary fibers are ingested, they give rise to perception of satiety since they reside for a prolonged period in the stomach and they reside for a short time in the intestine, thus they are useful as a natural ingredient of a low-calorie food for prevention from corpulence or obesity (Innan et al, "dietary fibers", pages 73 and 76, 1982, Daiichi Shuppan)

It is also reported that oligosaccharides mainly in the range of disaccharides to hexasaccharides, which are prepared from hydrolysis of Konnyaku powder, are effective to promote growth of intestinal Bifidobacteria (Unexaminded Patent Application Gazzette No. 58-212780).

PROBLEMS IN THE PRIOR ART

Although Konnyaku powder has many useful effects as mentioned above, it has some deffects as follows:

(1) During processing of an aqueous solution of Konnyaku powder, the solution tend to be highly viscous to form a gel.

(2) Use of Konnyaku powder is restricted due to its undesirable flavor and taste.

(3) Konnyaku powder has a property of adsorbing minerals which are essential for human nutrition, thus when Konnyaku powder is ingested along with other foods or a food containing Konnyaku powder is ingested, calcium is adsorbed to Konnyaku in the foods. This may result in obstruction of calcium absorption in the digestive tract or in a negative nutritional calcium ballance which in turn result in decrease in minerals in the bones to cause osteomalacia (Oku et al, Journal of Nutrition, Vol. 112, Page 410, 1982).

According to the results of the study by the inventors, the osmotic pressure of 20% aqueous solution of oligosaccharides, mainly comprising di- or trisaccharides (average molecular weight 400) which are obtained by hydrolysis of Konnyaku powder, is up to 500 m Osm/kg $H_2O$ which exceeds that of human body fluid, 285 m Osm/kg $H_2O$. Aqueous solution of Konnyaku powder reaches to the large intestine retaining large quantity of water which may result in a symptom of diarrhea. Therefore, it is required to restrict a dose of such oligosaccharides within a prescribed level.

The inventors of the present invention have conducted a study on dietary fibers and found that an aqueous solution of partially hydrolyzed Konnyaku powder has a relatively low osmotic pressure which do not cause diarrhea, and do not lead to decrease in calcium content in the bones. The present invention is based on the discovery.

SOLUTION OF THE PROBLEMS

According to the method of the present invention, partially hydrolyzed Konnyaku powder, having average molecular weight of 2,000–15,000, can be prepared by suspending Konnyaku powder in water, then partially hydrolyzing the polysaccharides included therein with a cellulase. The resulted products has various favorable functions referred in the above while eliminating the defects of non-hydrolyzed Konnyaku powder and exhaustively hydrolyzed.

PURPOSE OF THE INVENTION

Therefore, it is an object of the present invention to provide dietary fibers which can be widely utilized for food industry while retaining the favorable functions of intact dietary fibers of Konnyaku powder but eliminating the adverse effects thereof. More particularly, it is an object of the present invention to provide dietary fibers which can be widely utilized for preparation of processed foods which do not cause diarreha due to its moderate osmotic pressure.

It is another object of the present invention to provide a method for preparation of such water-soluble dietary fibers.

DETAILED DESCRIPTION OF THE INVENTION

Konnyaku powder, which can be utilized as the raw material in the present invention may be fine powder, sieved powder to medium particle size or coarse powder. Konnyaku powder may bhe declorized and deodorized with alcohl. Glucomannan, isolated from pulverized Konnyaku tubers, is also utilized.

Any enzymes, which may hydrolyse glucomannan, can be utilized in the present invention, for example, Cellulase derived from *Aspergillus niger*, *Trichoderma viride* and *Penicillium notatum*; mannanase derived from the genus of Streptomyces, *Rhizopus niveus*, *Bacillus circulans* and Streptomyces, *Rhizopus niveus*, *Bacillus circulans* and tuberous roots of Konnyaku. Among the enzymes which hydrolyse a $\beta$-glucoside bond in a molecule of glucomannan (endo-type), cellulases derived from microorganisms belonging to the genus of Aspergillus are preferable which hydrolyse endo-$\beta$-glycosidic linkage (endo-type). Reaction time and pH of enzymatic reaction may exert large influences to the yield of the reaction products and molecular weights thereof. Most of enzyme preparations available in the market are mixtures of exo-type enzyme such as exo-1,4-$\beta$-D-glucanase, endo-type enzyme such as endo-1,4-$\beta$-D-glucanase and $\beta$-glucosidase. Thus it is necessary to determine the preferable reaction time, temperature and pH so as to perform enzymatic reaction under the conditions where the activity of exo-type enzyme is lowered to minimize the production of monosaccharides and oligosaccharides.

For example, typical conditions for enzymatic reaction will be 40° C. for 4–16 hours or 55° C. for 4 hours as shown in examples 1–5. The resulted reaction products are heated for inactivation of enzymes, the supernatant liquid thereof is collected, the collected liquid is subjected to condensation with or without performing demineralization, decolorization and deodorization, and further subjected to drying to obtain powdery product of water-soluble dietary fibers.

The dietary fibers in accordance with the present invention can be ingested as it is or they can be added to various foods without changing the properties thereof. For example, they can be added not only to solid foods such as frozen desserts, breads and jelly but also to liquid foods or drinkables such as milk, fruit juice and the like.

Some exemplified tests will be described hereinafter.

TEST 1 [OSMOTIC PRESSURE TEST]

(1) Materials

Three kinds of 20% aqueous solution of water-soluble dietary fibers having different average molecular weights (test samples), prepared in the same manner as stated in Examples 1, 2 and 4, and a 20% aqueous solution of acid hydrolyzate (control sample), having average molecular weight of 400 obtained by hydrolysis of Konnyaku powder, were prepared to test.

(2) Method

Osmotic pressures of the test and the control samples were measured by the conventional method.

(3) Results

The results are shown in Table 1.

TABLE 1

| OSMOTIC PRESSURES OF DIETARY FIBERS | |
|---|---|
| Samples of dietary fibers | Osmotic Pressure (m Osm/kg $H_2O$) |
| Test sample corres. to Example 1 (average molecul. weight 15,000) | 100 |
| Test sample corres. to Example 2 (average molecul. weight 7,000) | 120 |
| Test sample corres. to Example 4 (average molecul. weight 2,000) | 135 |
| Control sample of acid hydrolyzate (average molecul. weight 400) | 502 |

The osmotic pressures of the test samples (water-soluble dietary fibers in accordance with the present invention) were lower than that of control sample and that of human body fluid (285 m Osm/kg $H_2O$), and therefore ingestion of the dietary fibers in accordance with the present invention never cause diarrhea.

TEST 2 [TEST TO ASSES THE EFFECT FOR CALCIUM DEPOSIT IN THE BONES]

(1) Materials

The modified basic diet was used for feeding rats. The composition of the diet, used as test diet in this test, was basically the same with that of the basic diet except that a portion of 20% of corn starch was substitued with the corresponding quantity of the water-soluble dietary fibers (average molecular weight 15,000) prepared from commarcially available Konnyaku powder by the method set forth in Example 1 of the present invention. The composition of the control diet used in this test was basically the same with that of the basic diet except that a 20% portion of corn starch in the basic diet was substituted with the intact Konnyaku powder without being subjected to hydrolysis. The details of the compositions of these diet feeds are shown in Table 2.

(2) Method

The three groups (A, B and C) of test animals each comprising 6 Wister rats, were fed the three kinds of diet feeds respectively for 8 weeks then ash contents of the bones of the test animals were measured in accordance with the conventional method. The mean values and the standard deviations of the ash content (%) in the bones of the animals belonging to the respective groups were calculated in accordance with the conventional method.

(3) Results

The results are shown in Table 2.

TABLE 2

EFFECTS OF KONNYAKU POWDER AND THE WATER SOLUBLE DIETARY FIBERS TO SKELETAL ASH CONTENT

| | percentage of the components in the feeds | | |
|---|---|---|---|
| components of feeds | groupe A test feed | groupe B basic feed | groupe C control |
| corn starch | 47 | 67 | 47 |
| water-soluble diet. fiber corres. to Example 1 | 20 | — | — |
| Konnyaku powder | — | — | 20 |
| casein | 21 | 21 | 21 |
| corn oil | 7 | 7 | 7 |
| mineral salts mixture | 4 | 4 | 4 |
| vitamines mixture | 1 | 1 | 1 |
| skeletal ash content (%) | 62.0 ± 0.5 | 61.5 ± 0.5 | 54.5 ± 0.6 |

It was observed that skeletal ash content of the animals was almost the same in group A (test feed) and B (basic feed), and that ash content was lower in group C (control feed) compared with group A and B.

Skeletal ash content is directly proportional to calcium content thereof.

It is conceived that addition of Konnyaku powder to feed is to decrease skeletal ash content while addition of the water-soluble dietary fibers in accordance with the present invention do not affect skeletal ash content.

TEST 3 [TEST RELATING DIARRHEA]

(1) Materials

Aqueous solution of water-soluble dietary fibers in a a concentration of 15%, prepared in accordance with the method set forth in Example 4 (average molecular weight 2,000), was used.

(2) Method

One hundred gram portion of the aqueous solution (15 g of water-soluble dietary fibers) were administrated to 12 healthy adult subjects (22–50 years old, comprising 6 men and 6 women) for 7 days, and their stools were observed on the next day of the last day of the period for administration.

(3) Result

The results are shown in Table 3.

TABLE 3

| OBSERVATION OF STOOLS | |
|---|---|
| features | number of persons |
| hard stool | 1 |
| normal stool | 11 |
| diarrhea | 0 |
| total | 12 |

It was concluded that panels never alleged diarrhea and 90% of panels had normal stools after uptake of the dietary fibers of the present invention for 7 days.

TEST 4 [DIETARY FIBER CONTENT]

(1) Materials

Samples 1, 2 and 3 of the dietary fibers, respectively prepared from commercially available Konnyaku powder in the same manner set forth in Examples 1, 2 and 4, and the intack Konnyaku powder were subjected to determination.

(2) Method

The dietary fibers content in the respective materials was measured by Prosky's method (Prosky et al, Journal of the Association of Official Analytical Chemistry, Vol. 67, page 1044, 1984).

(3) Results

The results are shown in Table 4.

TABLE 4

| DIETARY FIBERS CONTENT | | |
|---|---|---|
| sample numbers | average molecular weight | dietary fiber content (%) |
| 1 corres. to Example 1 | 15,000 | 92.4 |
| 2 corres. to Example 2 | 7,000 | 90.8 |
| 3 corres. to Example 4 | 2,000 | 87.5 |
| Konnyaku powder | — | 80.2 |

From Table 4, it is evident that the water-soluble dietary fibers in accordance with the present invention retains the characteristics of dietary fibers even after treatment of afford watr solubility.

TEST 5 [PANEL TEST FOR APPLICABILITY TO FROZEN CONFECTIONARY]

(1) Materials

Having used the ingredients shown hereunder, frozen confectionary was prepared in accordance with the conventional method.

| materials | Ingredients test sample | control sample |
|---|---|---|
| sweetened condensed milk | 16.3 (g) | 16.3 (g) |
| unsalted butter | 10.1 | 10.1 |
| skim milk powder | 5.7 | 5.7 |
| corn syrup | — | 5.5 |
| artificial sweetener | 0.04 | — |
| water-soluble dietary fibers (corres. to Example 1) | 5.5 | — |
| emulsifier/stabilizer | 0.5 | 0.5 |
| seasonings | 0.132 | 0.132 |
| colorings | 0.012 | 0.012 |
| water | 61.716 | 61.756 |
| total | 100.0 | 100.0 |

It should be noted that the test samples contained the water-soluble dietary fibers (average molecular weight 15,000) prepared in accordance with the method set forth in Example 1, while the control samples contained corn sylup instead of the water-soluble dietary fibers.

(2) Method

Three samples consisting of paired test samples and one control sample, or paired control samples and one test sample were given to each of 40 panelars consisting of 20 women and 20 men. In order to asses the panel's perceptible reliability, they are assigned to distinguish one odd sample in those uniformed stimuli which are composed of two identical and one odd samples (triangle test). They are also instructed to declare one sample which they prefer most among the paired two and one odd samples (Paired-comparison test).

The panels who correctly distinguished the single distinct sample were eligible to be qualified panels (Motosaburo Motoyama et al, "Application of stochastics to chemistry and biology" Vol. 3, page 145, Nankohdoh, June 1961).

(3) Results

The results of the test are shown in Table 5.

TABLE 5

| PANEL TEST FOR FROZEN CONFECTIONARY | | | | | |
|---|---|---|---|---|---|
| panelar | | triangle test | | paired-comparison test | |
| sex | number | qualfied panels | unqualified | prefer test sample | prefer control sample |
| men | 20 | 18 | 2 | 8 | 10 |
| women | 20 | 16 | 4 | 9 | 7 |
| total | 40 | 34 | 6 | 17 | 17 |

From the results shown in Table 5, the panels were recognized to be qualified to distinguish the test samples from the control samples, and the number of those panels who preferred test samples and those who preferred control samples were almost the same.

TEST 6 [PANEL TEST FOR APPLICABILITY TO COOKIES]

(1) Materials

With the recipe shown hereunder, the test and the control samples of cookies were prepared.

| materials | test samples | control samples |
| --- | --- | --- |
| weak flour | 50 (g) | 50 (g) |
| butter | 40 | 40 |
| sugar | 20 | 20 |
| egg | 10 | 10 |
| water soluble dietary fibers | 10 | — |
| total | 140 | 130 |

The test samples contained water-soluble dietary fibers (average molecular weight 7,000) prepared in the same manner as set forth in Example 2, and the dietary fibers were omitted in the control samples.

(2) Method

In the same manner as in Test 5, Triangle test and Paired-comparison test were conducted.

(3) Results

The results are shown in Table 6.

TABLE 6

| panelar | | Triangle test | | Paired-comparison test | |
| --- | --- | --- | --- | --- | --- |
| sex | number | qualifed panels | unqualified | prefer test sample | prefer control |
| men | 20 | 19 | 1 | 9 | 10 |
| women | 20 | 17 | 3 | 8 | 9 |
| total | 40 | 36 | 4 | 17 | 19 |

From the results shown in Table 6, cookies of test samples were distinguishable from those of control samples, but substantial difference was not observed between the samples in Paired-comparison test.

TEST 7 [APPLICABILITY TO BREAD]

(1) Materials

With the receipe shown in the following table, breads for the test and the control samples were prepared.

| materials | test samples | control samples |
| --- | --- | --- |
| strong flour | 280 (g) | 280 (g) |
| sugar | 17 | 17 |
| salt | 5 | 5 |
| butter | 11 | 11 |
| skim milk powder | 6 | 6 |
| yeast | 3 | 3 |
| water-soluble dietary fibers | 20 | — |
| water | 210 | 210 |
| total | 552 | 532 |

The test samples contained dietary fibers (average molecular weight 2,000), prepared in the same manner as in Example 4, and the control samples did not contain dietary fibers.

(2) Method

As in Test 5, Triangle test and Paired-comparison test were conducted with respect to the breads of test and control samples.

(3) Results

The results of the tests are shown in Table 7.

TABLE 7

| PANEL TEST OF BREADS | | | | | |
| --- | --- | --- | --- | --- | --- |
| panelar | | Triangle test | | Paired-comparison test | |
| sex | number | qualified panels | unqualified | prefer test sample | prefer control |
| men | 20 | 17 | 3 | 8 | 9 |
| women | 20 | 18 | 2 | 10 | 8 |

TABLE 7-continued

| PANEL TEST OF BREADS | | | | | |
| --- | --- | --- | --- | --- | --- |
| panelar | | Triangle test | | Paired-comparison test | |
| sex | number | qualified panels | unqualified | prefer test sample | prefer control |
| total | 40 | 35 | 5 | 18 | 17 |

The breads of the test samples were distinguishable from those of the control samples, but substantial difference was not observed between the both samples in Paired-comparison test.

TEST 8 [APPLICABILITY TO JUICE AND MILK]

(1) Materials

With the recipe shown in the following tables, the test and control samples of fruit juice and milk were respectively prepared.

| materials | test samples | control |
| --- | --- | --- |
| Ingredients of Fruit Juice | | |
| 100% orange juice | 95 (g) | 95 (g) |
| water-soluble dietary fibers | 5 | — |
| water | — | 5 |
| total | 100 | 100 |
| Ingredients of Milk | | |
| cow's milk* | 95 (g) | 95 (g) |
| water-soluble dietary fibers | 5 | — |
| water | — | 5 |
| total | 100 | 100 |

*non-fat milk solids content: more than 8.3%, milk fat content: more than 3.5%

The test samples of fruit juice and milk respectively contained dietary fibers (average molecular weight 15,000) prepared in the same manner as in Example 1, and the control samples thereof did ot contain fibers.

(2) Method

As in Test 5, Triangle test and Paired-comparison test were conducted with respect to the fruit juice and milk of the test and the control samples.

(3) Results

No precipitation was observed in all the samples of both of fruit juice and milk.

The results of the panel tests are shown in Tables 8 (for fruit juice) and 9 (for milk).

TABLE 8

| PANEL TEST OF FRUIT JUICE | | | | | |
| --- | --- | --- | --- | --- | --- |
| panelar | | Triangle test | | Paired-comparison test | |
| sex | number | qualified panels | unqualified | prefer test sample | prefer control |
| men | 20 | 17 | 3 | 9 | 8 |
| women | 20 | 16 | 4 | 8 | 8 |
| total | 40 | 33 | 7 | 17 | 16 |

TABLE 9

| PANEL TEST OF MILK | | | | | |
| --- | --- | --- | --- | --- | --- |
| panelar | | Triangle test | | Paired-comparison test | |
| sex | number | qualified panels | unqualified | prefer test sample | prefer control |
| men | 20 | 18 | 2 | 10 | 8 |
| women | 20 | 19 | 1 | 9 | 10 |

TABLE 9-continued

| | | PANEL TEST OF MILK | | | |
|---|---|---|---|---|---|
| | | Triangle test | | Paired-comparison test | |
| panelar | | qualified | | prefer | prefer |
| sex | number | panels | unqualified | test sample | control |
| total | 40 | 37 | 3 | 19 | 18 |

The test samples of fruit juice and milk were distinguishable from those of control samples, but substantial differences were not observed between the both samples in Paired-comparison test.

EXAMPLE 1

To 80 l of phosphate buffer solution (pH: 6.5), 67 g of cellulase A (trade name, purchased from Amano Seiyaku, Co., Ltd. JAPAN, specific activity: 15,000 U/g), derived from the microorganisms belonging to the genus of Aspergillus was added. The resulted mixture was heated to 40° C., and 4.0 kg of commercially available Konnyaku powder was added thereto and agitated to form a solution. The resultive resolution was allowed to stand at 40° C. for 4 hours to effect enzymatic hydrolysis, then the hydrolysed solution was heated to 100° C. for 10 minutes to stop the enzymatic reaction. The resultant mixture was subjected to centrifugation at 6,000 G, and the supernatant fraction was collected. The collected supernatant was successively passed through cation exchanged resin column to the volume of 1,000 ml (Dowex 50 W×8; H+ type) and anion exchange resin column (Dowex 1×8; OH− type) to the volume of 4,000 ml for demineralization. The demineralized reaction mixture was condensed and subsequently spray dried to obtain about 1,250 g of dried dietary fibers. The average molecular weight of the dietary fibers was 15,000.

EXAMPLE 2

Soluble fibers, to a quantity of 2,250 g, were obtained in the same manner as described in Example 1, except that enzymatic reaction was carried out for 8 hours. The average molecular weight of the dietary fibers was 7,000.

EXAMPLE 3

Soluble dietary fibers, to a quantity of 2,650 g, were obtained in the same manner as described in Example 1, except that enzymatic reaction was carried out for 12 hours. The average molecular weight of the soluble dietary fibers was 3,000.

EXAMPLE 4

Soluble dietary fibers, to a quantity of 2,800 g, were obtained in the same manner as described in Example 1, except that enzymatic reaction was carried out for 16 hours. The average molecular weight of the dietary fibers was 2000,

EXAMPLE 5

To 30 l of acetate buffer solution (pH: 5.3), 13 g of cellulase Nagase (trade name, purchased from Nagase BioChemical Industry Co., Ltd., JAPAN, specific activity: 1,000 U/g), derived from the microorganisms belonging to the genus of Aspergillus was added. The resulted mixture was heated to 55° C., and about 1.33 kg of commercially available Konnyaku powder was added thereto and agitated to dissolve. In the same manner as in Example 1, except that the resultive solution was kept at 55° C. for 4 hours, about 740 g of dietary fibers was obtained. The average molecular weight of the dietary fibers was 5,000.

SIGNIFICANCE OF THE INVENTION

The significance of the invention are as follows:

1 The water-soluble dietary fibers of the present invention retain the desirable effects in the conventional dietary fibers such as cholesterol adsorbability and growth promoting activity of Bifidobacteria, while it is soluble in water which is favorable for application in the food industry.

2 The water-soluble dietary fibers of the present invention do not obstruct absorption of useful minerals such as calcium in the digestive tract.

3 The water-soluble dietary fibers of the present invention cause a relatively low osmotic pressure, and do not give rise to diarrhea even if an excess amount thereof is ingested.

4 The water-soluble dietary fibers of the present invention can be added to various types of foods and drinkables without affecting organoleptic characteristics thereof.

What is claimed is:

1. Water-soluble dietary fibers comprising partial hydrolyzate of polysaccharides of Konnyaku powder having average molecular weight ranging from 2,000 to 15,000.

2. A method for preparation of water-soluble dietary fibers comprising:
   dispersing Konnyaku powder in water;
   partially hydrolyzing polysaccharides of said Konnyaku powder with a cellulase which is derived from microorganisms belonging to the genus Aspergillus; and
   separating water-soluble dietary fibers having average molecular weight ranging from 2,000–15,000 from the reaction mixture.

* * * * *